Figure 1:
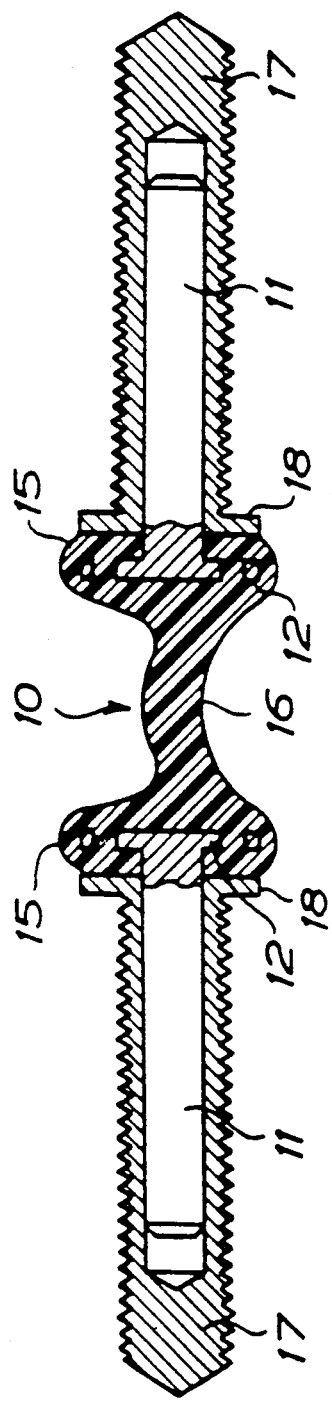

United States Patent [19]

Persson et al.

[11] Patent Number: 5,011,497
[45] Date of Patent: Apr. 30, 1991

[54] JOINT PROSTHESIS

[75] Inventors: Jan-Ove Persson, Höör; Per-Ingvar Branemark, Mölndal, both of Sweden

[73] Assignees: Atos Medical AB, Horby; Institutet for Tillampad Bioteknologi, Gothenburg, both of Sweden

[21] Appl. No.: 473,992
[22] PCT Filed: Oct. 28, 1988
[86] PCT No.: PCT/SE88/00580
 § 371 Date: May 2, 1990
 § 102(e) Date: May 2, 1990
[87] PCT Pub. No.: WO89/03663
 PCT Pub. Date: May 5, 1989

[30] Foreign Application Priority Data

Oct. 29, 1987 [SE] Sweden ............................ 8704211-5

[51] Int. Cl.5 .............................................. A61F 2/42
[52] U.S. Cl. .......................................... 623/21; 623/18
[58] Field of Search .................... 623/16, 17, 18, 19, 623/20, 21, 22, 23

[56] References Cited

U.S. PATENT DOCUMENTS

| | | | |
|---|---|---|---|
| 3,886,600 | 6/1975 | Kahn et al. | 623/21 |
| 4,204,284 | 5/1980 | Koeneman | 623/18 |
| 4,229,839 | 10/1980 | Schwemer | 623/18 |
| 4,229,840 | 10/1980 | Gristina | 623/21 |
| 4,352,212 | 10/1982 | Greene et al. | 623/21 |
| 4,367,562 | 1/1983 | Gauthier | 623/18 |
| 4,759,768 | 7/1988 | Hermann et al. | 623/21 |
| 4,946,378 | 8/1990 | Hirayama et al. | 623/17 |

Primary Examiner—David J. Isabella
Attorney, Agent, or Firm—Merchant & Gould

[57] ABSTRACT

Joint prosthesis comprising a joint section (10) having a web (16) of an elastomer, arranged between two pins (11) which are inserted each in one of two tubular screws (17) to be secured in the bones between which the joint prosthesis shall be arranged, the pins being secured in the web by means of flanges embedded into the elastomer. Pins and screws comprise a biocompatible material.

8 Claims, 2 Drawing Sheets

JOINT PROSTHESIS

The invention relates to a joint prosthesis comprising a joint section between two pins to be secured in the bones between which the joint prosthesis shall be mounted and comprising a web of an elastomer, forming a joint section between the pins, said pins being secured in the web by embedding them into the elastomer.

A finger joint prosthesis of this type is disclosed in U.S. Pat. No. 3,886,600 which describes an elbow-joint wherein two rigid pin-like end elements are connected to the elastomer web to be inserted into the medullary canal of the upper and lower arm bones, respectively.

U.S. Pat. No. 4,352,212 describes an embodiment wherein the joint section comprises two elements slidingly engaging each other, one of said elements forming a joint socket and the other one forming a joint pin which is articularely received by the joint socket. The pins on the two elements of the joint section are received in plastic plugs which shall be driven into the canal in the bones to be interconnected by means of the joint prosthesis.

There are also prior art joint prostheses (see e.g. U.S. Pat. No. 3,875,594) which in their entirety consist of an elastomer and by means of pins which accordingly form an integral part of the joint prosthesis, are secured in the bone canal. Such prostheses can be exposed to wear between pin and bone at existing joint articulation, and as a consequence thereof fine particles of the elastomer may penetrate into the human organism where such particles may cause infections and other trouble in different organs.

The object of this invention is to provide a joint of the kind referred to above, by means of which it is achieved that the joint prosthesis will be constructively simple, durable, and easily articulated, that no wear will arise, that a safe, permanent and harmless connecting to the bones is achieved, and that the joint prosthesis can be easily exchanged.

Said object is achieved according to the invention by the joint prosthesis having obtained the characterizing features of claim 1.

In order to explain the invention in more detail, further advantages achieved by the invention also being mentioned, reference is made to the accompanying drawings in which FIG. 1 is a side view, partly in vertical cross section, of a finger joint prosthesis according to the invention.

Figure 2:
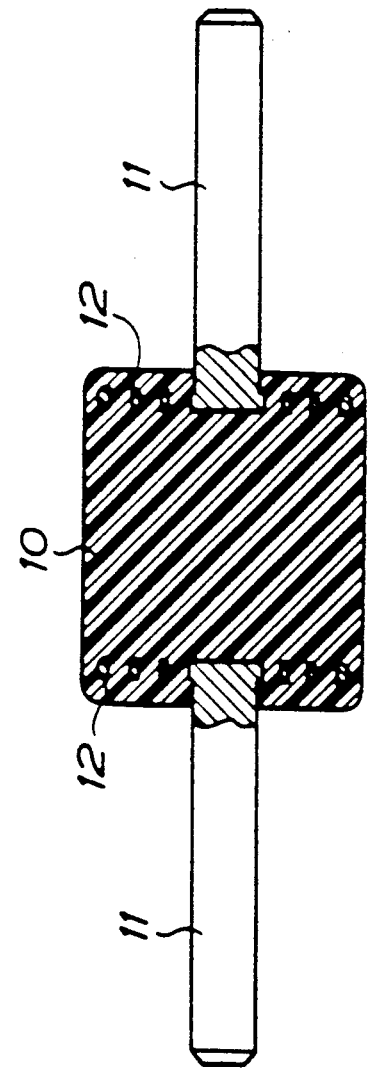
Figure 3:
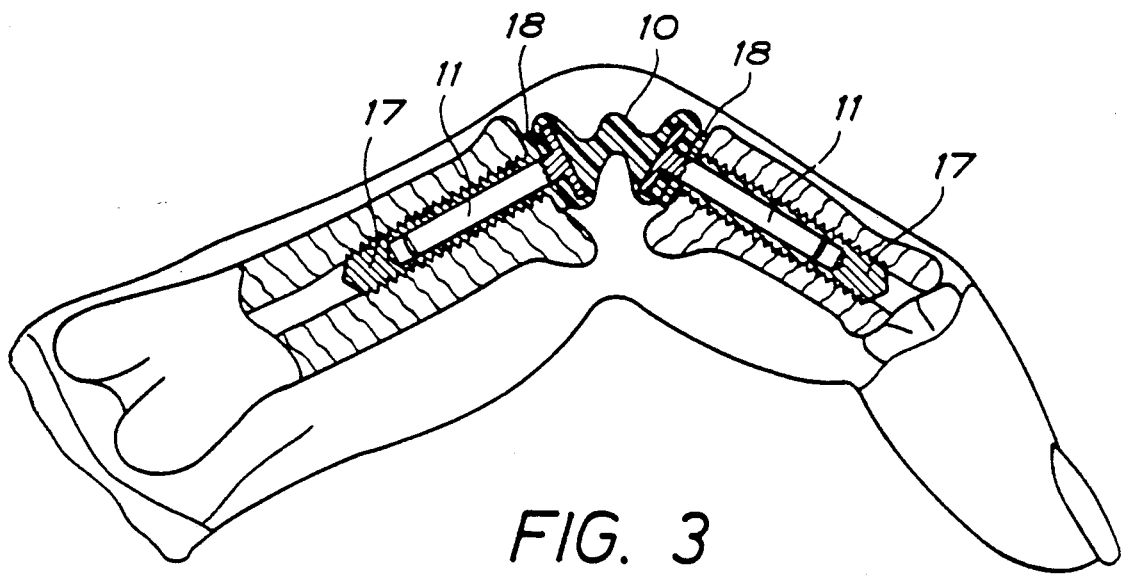
Figure 4:
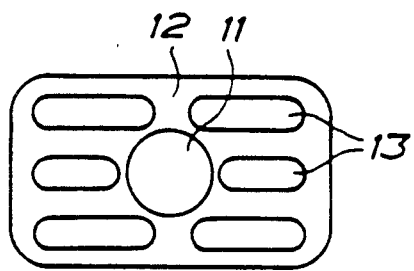
Figure 5:
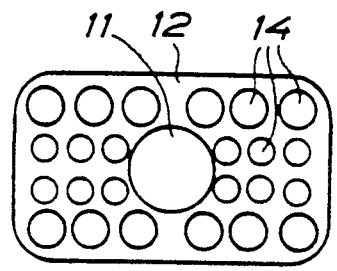
Figure 6:
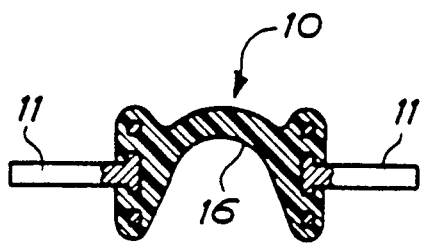

FIG. 2 is a plan view, partly in horizontal cross section, of the finger joint prosthesis in FIG. 1, FIG. 3 is a cross-sectional view showing the finger joint inserted by an operation between two bones, FIG. 4 is an end view of the attachment plate of the pin in one embodiment, and FIG. 5 is a corresponding view of another embodiment, and FIG. 6 discloses a modified embodiment of the joint section of elastomer in the same manner as FIG. 1.

Referring to FIGS. 1 to 5 the finger joint prosthesis shown therein comprises a joint section 10 of an elastomer which can comprise silicon rubber or polyurethane. This joint section is connected with two pins 11 of a biocompatible material, preferably titanium, which are secured in the joint section by the joint section being injection molded around end flanges 12 on the pins so that these end flanges are completely embedded into the elastomer. In order to obtain a satisfactory connection of the pins the flanges form either slots 13 according to FIG. 4 or apertures 14 according to FIG. 5 so that the elastomer during the injection molding can penetrate through these openings. The joint section forms two plate-shaped rectangular enlargements 15 around the flanges and forms between said flanges a relatively thin web 16 slightly curved.

Each pin 11 is inserted into a tubular screw 17 which should also consist of a biocompatible material and preferably is of the same kind as the pins, i.e. it should consist of titanium. The screw has an end flange 18, and is screwed into the canal in the bone wherein it is to be secured as shown in FIG. 3, until the flange engages the bone. The screw will grow on to the bone, which means that the bone will not deteriorate due to uneven loading and that the prosthesis can be exposed to larger loads for an extended period so that also younger patients with an active life can get a prosthesis which functions considerably better for a long time than prostheses of prior art embodiment. The bore in the screw is sufficiently long so that the pin will not touch the bottom therein when it is completely inserted into the bore. The mounting of the joint prosthesis is facilitated by the fact that the pins 11 can be pushed into the screws 17 after these having been secured in the bones. After the mounting the pins will be maintained in the screws by the elastic joint section 10 provided therebetween. The pins may be locked in the screws after mounting Since there is no movement between the pins and the screws when the prosthesis is being used, the wear of the prosthesis will be kept at minimum, which means that the life will be long and the risk for infections or irritations due to particles from the prosthesis penetrating into the tissues of the body, is eliminated practically completely. Another advantage is that the joint section with associated pins easily can be exchanged by a simple operation with the screws being left in the bones if the joint prosthesis for some reason should not function satisfactorily. The pin can be cylindrical so that it can be rotated in the screw, the prosthesis being more easily adjusted as a consequence thereof, but the rotatability also provides the risk of the prosthesis rotating from the proper position during the use thereon. Even if the rotatable embodiment will be cheaper than an embodiment wherein means are provided to prevent rotation, it may be preferred that the pin is guided in the bore in such a manner that it cannot be rotated therein. This can be achieved by a projection on the pin or in the bore being displaceably received in a groove in the bore or the pin, respectively, or by the pin and the bore having a suitable non-round shape. For example, the pin and the bore can have hexagonal cross-sectional shape, which provides the advantage that the screw can be tightened by means of a pin spanner engaging the bore of the screw. Otherwise it is necessary to provide a screw-driver slot in the screw or to provide a hexagonal flange thereon in order that the screw can be gripped for tightening.

Due to the elastic joint section 10 the joint prosthesis has spring back, which is important when rheumatic patients are being treated. Without spring back the fingers of the patient tend to get stiff in a bent position. Moreover, the elastic joint section takes up shocks and vibrations which are attenuated as a consequence thereof, increasing the strength of the prosthesis and the attachments thereof.

The joint section 10 can be shaped also in the manner shown in FIG. 6 according to which the web is thinner and the arch on the lower side of the web is higher. Such a joint is more suited than the joint of the embodiment first described to replace that part of the bone of the natural finger joint which forms the knuckle, but on the other hand can involve the drawback that tissue will grow into the high arch on the lower side thereof and then can interfere with the articulation by the tissue being clamped below the joint section, the web at the same time being exposed to greater tensile stress at the upper side thereof. However, it is possible to shape the web in different manners in order to adapt the finger joint prosthesis in the best possible way to the conditions at the place where it is to be inserted by an operation.

The joint prosthesis described can be manufactured at lower costs and in a simpler way than such prostheses which include elements slidingly engaging each other, which means that the prosthesis can be used in a larger category of patients that the more expensive joints.

The invention has been illustrated by describing a finger joint prosthesis but it should be stressed that the invention can be applied also to other joints of hinge type such as hand joints, armbow joints, and foot joints.

We claim:

1. A joint prosthesis configured to replace an existing joint comprising:
   an elastomeric webbed joint section;
   two screws with bores at ends adjacent to the elastomeric webbed joint section, the screws configured to be received in the respective bones adjacent the joint;
   two elongated pins characterized in that each pin has at one end thereof a transverse flange, said flanges being embedded into opposite sides of the webbed joint section, and wherein each of said pins is adapted to be inserted into the bores of respective hollow screws.

2. A joint prosthesis as in claim 1, wherein the webbed joint section has at least one curved surface.

3. Joint prosthesis as in claim 1 wherein the flanges (12) are apertured.

4. Joint prosthesis as in claim 3, further including an injection-molded webbed joint section (10) adapted to cooperate with the apertures of the flanges.

5. Joint prosthesis as in claim 1 wherein the pins (11) are rotatably mounted in the screws (17).

6. Joint prosthesis as in claim 1 wherein the pins (11) are non-rotatably guided in the screws (17).

7. Joint prosthesis as in claim 6 wherein the pins (11) and bores in the screws (17), receiving said pins, have non-round cross-sectional shape.

8. Joint prosthesis as in claim 1 wherein the pins (11) and the screws (17) consist of titanium.

* * * * *

UNITED STATES PATENT AND TRADEMARK OFFICE
CERTIFICATE OF CORRECTION

PATENT NO. : 5,011,497

DATED : April 30, 1991

INVENTOR(S) : Jan-Ove Persson et al

It is certified that error appears in the above-identified patent and that said Letters Patent is hereby corrected as shown below:

Col. 1, line 20, "articularely" should read --articulately--.

Col. 2, line 29, insert --.-- after the word "mounting".

Col. 2, line 44, "thereon" should read --thereof--.

Signed and Sealed this

Ninth Day of March, 1993

Attest:

STEPHEN G. KUNIN

Attesting Officer

Acting Commissioner of Patents and Trademarks